United States Patent
Weber

(10) Patent No.: US 7,435,854 B2
(45) Date of Patent: *Oct. 14, 2008

(54) METHODS FOR PREPARING O-DESMETHYLVENLAFAXINE

(75) Inventor: Beat Theodor Weber, Zofingen (CH)

(73) Assignee: Wyeth, Madison, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 11/756,772

(22) Filed: Jun. 1, 2007

(65) Prior Publication Data

US 2007/0225525 A1 Sep. 27, 2007

Related U.S. Application Data

(63) Continuation of application No. 10/750,196, filed on Dec. 31, 2003, now abandoned, which is a continuation of application No. 10/304,871, filed on Nov. 26, 2002, now Pat. No. 6,689,912.

(60) Provisional application No. 60/334,953, filed on Dec. 4, 2001.

(51) Int. Cl.
*C07C 211/00* (2006.01)

(52) U.S. Cl. ...................... 564/336; 564/409

(58) Field of Classification Search ........ None
See application file for complete search history.

(56) References Cited

U.S. PATENT DOCUMENTS

| 4,535,186 A | 8/1985 | Husbands et al. |
| 4,729,817 A | 3/1988 | Francis et al. |
| 5,043,466 A | 8/1991 | Shepard |
| 6,441,048 B1 | 8/2002 | Jerussi et al. |
| 6,689,912 B2 * | 2/2004 | Weber .................. 564/336 |
| 2004/0158101 A1 | 8/2004 | Weber |

FOREIGN PATENT DOCUMENTS

| WO | WO 00/59851 | 10/2000 |
| WO | WO 00/76955 | 12/2000 |
| WO | WO 02/06453 | 1/2002 |
| WO | WO 02/064543 | 8/2002 |

OTHER PUBLICATIONS

* Julia W. Wildes et al., J. Org. Chem., 1971, 721-723, 36(5).
International Application No. PCT/US02/38403 PCT Written Opinion.
International Application No. PCT/US02/38403 PCT International Preliminary Examination Report.
International Application No. PCT/US02/38403 PCT International Search Report.

* cited by examiner

*Primary Examiner*—Samuel A Barts
(74) *Attorney, Agent, or Firm*—Julie Anne Knight; Charles E. Lyon; Choate Hall & Stewart LLP

(57) ABSTRACT

The present invention provides an efficient method of making O-desmethyl-venlafaxine.

20 Claims, No Drawings

METHODS FOR PREPARING O-DESMETHYLVENLAFAXINE

This application is a continuation of application Ser. No. 10/750,196, filed on Dec. 31, 2003 (now abandoned), which is a continuation of application Ser. No. 10/304,871, filed on Nov. 26, 2002 (now U.S. Pat. No. 6,689,912), which claims priority from co-pending provisional application Ser. No. 60/334,953, filed on Dec. 4, 2001, the entire disclosure of each of these priority applications is hereby incorporated by reference.

BACKGROUND OF THE INVENTION

O-desmethylvenlafaxine is a major metabolite of venlafaxine. Methods to make O-desmethylvenlafaxine are described in U.S. Pat. No. 4,535,186. This method uses benzyl blocking groups leading to relatively low throughput.

A process of making O-desmethylvenlafaxine is also described in WO 00/59851 in which venlafaxine is allowed to react with diphenyl phosphide in THF (generated by adding n-butyl lithium in THF to diphenylphosphine in THF below 0° C.) at reflux for an overnight period. The yield was reported to be 73.8%. Furthermore, the method involved extraction steps involving large volumes of solvent.

The present invention provides a process of making O-desmethylvenlafaxine which is both time and material efficient.

DESCRIPTION OF THE INVENTION

In accordance with the present invention is provided a method of making O-desmethylvenlafaxine comprising the steps of demethylating a compound of Formula I to provide a compound of Formula II as described in Scheme I.

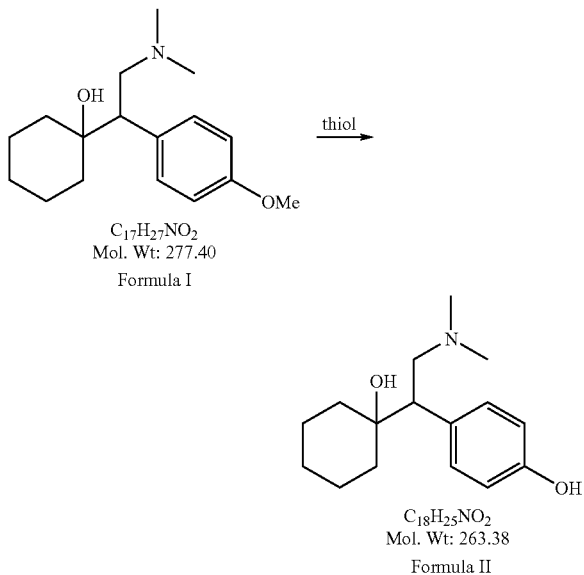

Scheme I $C_{17}H_{27}NO_2$
Mol. Wt: 277.40
Formula I $C_{18}H_{25}NO_2$
Mol. Wt: 263.38
Formula II As described in Scheme I the starting material, venlafaxine (Formula I), is demethylated. Venlafaxine may be prepared in accordance with procedures known in the art such as described in U.S. Pat. No. 4,535,186.

In accordance with the present invention, demethylation is performed using a high molecular weight alkane, arene, or arylalkyl thiolate anion, such as straight or branched chain alkane thiolate anions having 8 to 20 carbon atoms, mono or bicyclic arene thiolate anions having 6 to 10 carbon atoms, or mono or bicyclic arylalkyl thiolate anions having 7 to 12 carbon atoms in the presence of a protic or aprotic solvent. Optionally, a base such as an alkoxide comprised of a straight or branched chain alkyl group of from 1 to 6 carbon atoms may be present to generate the thiolate anion.

Preferably the aliphatic thiol has from 10 to 20 carbon atoms and most preferably the aliphatic thiol is dodecanethiol. The aromatic thiol is preferably benzenethiol. The arylalkyl thiolate anion is preferably toluenethiol or naphthylmethanethiol.

When present, the alkoxide is preferably a lower alkoxide (methoxide, ethoxide and the like) such as sodium methoxide (sodium methylate, sodium methanolate).

The solvent is preferably a hydroxylic or ethereal solvent, and more preferably an alcohol, ethylene glycol or ether of ethylene glycol. Ethers of ethylene glycol include, but are not limited to, ethylene glycol monoethyl ether, triethylene glycol dimethyl ether and polyethylene glycol. Preferably, the solvent is an inert, polar, high boiling point ether of ethylene glycol such as polyethylene glycol and most preferably PEG 400 (polyethylene glycol having a molecular weight range of from about 380-420).

The reaction is performed at a temperature of from about 150° C. to about 220° C., more preferably from about 170° C. to about 220° C., and most preferably from about 180° C. to about 200° C. The reaction is generally allowed to progress until, ideally, not more than 1% venlafaxine remains. In some aspects of the invention the reaction is complete in from about 2 hours to about 5 hours and more preferably in from about 2 to about 3.5 hours.

The thiolate anion can be prepared separately or in situ. In some preferred embodiments of the present invention, venlafaxine base is dissolved in polyethylene glycol 400 containing dodecanethiol and sodium methylate as a solution in methanol as the temperature is increased to from about 180° C. to about 200° C., with stirring for about 2 to about 3.5 hours. In other preferred embodiments of the present invention, venlafaxine base is dissolved in polyethylene glycol containing dodecanethiolate and stirred for about 2 to about 3.5 hours at from about 180° C. to about 200° C. with stirring.

Thereafter the reaction mixture is cooled to between about 65° C. and about 75° C. and an alcohol may be added as a diluent before neutralization to the isoelectric point (about pH9.5 to about pH10.0) with an appropriate neutralization agent such as hydrochloric acid. The alcoholic medium may also aid in the crystallization of the product as neutralization is initiated.

Preferably the alcohol comprises a straight or branched chain alkyl group of 1 to 6 carbon atoms, such as methanol, ethanol, isopropanol, butanol, and the like, and mixtures thereof. In some preferred embodiments of the invention, the alcohol is isopropanol.

Yields of the present invention are greater than about 75% and generally from about 85% to greater than 90%.

The following Examples are illustrative but are not meant to be limiting of the present invention.

EXAMPLE 1

Dodecanethiol (122 g), venlafaxine (111 g), and a methanolic solution of sodium methanolate (30%, 90 g) and PEG 400 are heated to 190° C. The methanol is distilled off and the solution is stirred 2 h at 190° C. Then the temperature is lowered, 2-propanol (450 g) is added and the pH is adjusted to 9.5 with aqueous HCl. The precipitate is collected by suction filtration, and the cake is washed with 2-propanol, toluene, 2-propanol and water. The wet O-desmethylvenlafaxine is dried in vacuo.

Yield: 87 g.

$^1$H-NMR: (Gemini 200, Varian, 200 MHz) (DMSO-d6) δ=9.11 (s, br, 1H; OH), 6.98 (d, br, J=8.4, 2H; arom.), 6.65 (d, br, J=8.4, 2H; arom.), 5.32 (s, br, 1H; OH), 3.00 (dd, J=12.3 and 8.5, 1H), 2.73 (dd, J=8.5 and 6.3, 1H), 2.36 (dd, J=12.3 and 6.3, 1H), 2.15 (s, 6H, 2×Me), 1.7-0.8 (m, 10H, c-hex).

EXAMPLE 2

Venlafaxine (5.6 g) and benzenethiol sodium salt (6.9 g) are charged to PEG 400 (25 g). The reaction mixture is heated to 160° C. for 5 h. Then the temperature is lowered and water is added (60 g). The pH is adjusted to 3.5 with $H_3PO_4$. The organic by-products are removed by extraction with heptanes (25 g). The pH of the aqueous layer is then adjusted to 9.5 with aqueous ammonia. The precipitate is collected by suction filtration, re-slurried in water (100 g), isolated by suction filtration and dried in vacuo.

Yield 1 g.

$^1$H-NMR: (Gemini 200, Varian, 200 MHz) (DMSO-d6) δ=9.11 (s, br, 1H; OH), 6.98 (d, br, J=8.4, 2H; arom.), 6.65 (d, br, J=8.4, 2H; arom.), 5.32 (s, br, 1H; OH), 3.00 (dd, J=12.3 and 8.5, 1H), 2.73 (dd, J=8.5 and 6.3, 1H), 2.36 (dd, J=12.3 and 6.3, 1H), 2.15 (s, 6H, 2×Me), 1.7-0.8 (m, 10H, c-hex).

EXAMPLE 3

Dodecanethiol (69 g) venlafaxine (55 g) and an ethanolic solution of sodium ethanolate (21%, 82 g) are charged to a pressure vessel. The temperature is raised to 150° C. and the reaction mixture is stirred for 2 days. Then the temperature is lowered and the solution is filtered. The pH of the filtrate is adjusted to 9.5 with aqueous hydrogen chloride. The crystals are collected by suction filtration. The cake is washed with ethanol and dried in vacuo.

Yield: 42 g $^1$H-NMR: (Gemini 200, Varian, 200 MHz) (DMSO-d6) δ=9.11 (s, br, 1H; OH), 6.98 (d, br, J=8.4, 2H; arom.), 6.65 (d, br, J=8.4, 2H; arom.), 5.32 (s, br, 1H; OH), 3.00 (dd, J=12.3 and 8.5, 1H), 2.73 (dd, J=8.5 and 6.3, 1H), 2.36 (dd, J=12.3 and 6.3, 1H), 2.15 (s, 6H, 2×Me), 1.7-0.8 (m, 10H, c-hex).

EXAMPLE 4

Step a—Formation of the Reagent Sodium Dodecanethiolate.

Dodecanethiol (246 g) and sodium methylate in methanol 30% (216 g) are charged to a rotary evaporator. Vacuum is applied and the solvent is abstracted completely using a bath temperature up to 90° C. The remaining sodium dodecanethiolate (272 g) is used without further purification in the subsequent step.

Step b—Demethylation

A mixture of sodium dodecanethiolate (272 g) venlafaxine (256 g) and PEG 400 (185 g) is stirred 3 h at 190° C. Then the temperature is lowered and 2-propanol (915 g) is added and the pH is adjusted to 9.5 with aqueous HCl. The precipitate is collected by suction filtration, and the cake is washed with 2-propanol and water. The wet O-desmethylvenlafaxine is dried in vacua. Yield: 200 g.

$^1$H-NMR: (Gemini 200, Varian, 200 MHz) (DMSO-d6) δ=9.11 (s, br, 1H; OH), 6.98 (d, br, J=8.4, 2H; arom.), 6.65 (d, br, J=8.4, 2H; arom.), 5.32 (s, br, 1H; OH), 3.00 (dd, J=12.3 and 8.5, 1H), 2.73 (dd, J=8.5 and 6.3, 1H), 2.36 (dd, J=12.3 and 6.3, 1H), 2.15 (s, 6H, 2×Me), 1.7-0.8 (m, 10H, c-hex).

What is claimed:

1. A method of preparing O-desmethylvenlafaxine which comprises reacting venlafaxine with a high molecular weight alkane, arylalkyl or arene thiolate anion in a hydroxylic or ethereal solvent, or mixture thereof, to provide O-desmethylvenlafaxine.

2. The method of claim 1 wherein the solvent is an alcohol, ethylene glycol, ether of ethylene glycol, or mixture thereof.

3. The method of claim 1 wherein the solvent is ethylene glycol monoethyl ether, triethylene glycol, dimethyl ether or polyethylene glycol.

4. The method of claim 1 wherein the solvent is polyethylene glycol 400.

5. The method of claim 1 wherein the reaction is performed at about 150° C. to about 220° C.

6. The method of claim 1 wherein the reaction is performed at from about 170° C. to about 220° C.

7. The method of claim 1 wherein the reaction is performed at from about 180° C. to about 200° C.

8. The method of claim 1 wherein the reaction is carried out for about 2 to about 5 hours.

9. The method of claim 1 wherein the thiolate anion is a straight or branched chain alkane thiolate anion having 8 to 20 carbon atoms.

10. The method of claim 1 wherein the alkane thiolate anion is dodecanethiolate.

11. The method of claim 1 wherein the thiolate anion is an arene thiolate anion having from 6 to 10 carbon atoms.

12. The method of claim 11 wherein the arene thiolate anion is benzenethiolate.

13. The method of claim 1 wherein the thiolate anion is generated in the presence of an alkoxide.

14. The method of claim 13 wherein the alkoxide is methoxide.

15. The method of claim 1 which is carried out in a stoichiometric excess of thiolate:venlafaxine up to about 3.0:1.

16. The method of claim 15 in which the molar ratio of thiolate:venlafaxine is from about 1.15:1 to about 2.5:1.

17. The method of claim 1 further comprising neutralizing the product to the isoelectric point in the presence of an alcohol comprising a straight or branched chain alkyl group of from 1 to 6 carbon atoms.

18. The method of claim 17 wherein the alcohol is isopropanol.

19. The method of claim 17 in which the reaction mixture is cooled to between about 65° C. and about 75° C. before the an alcohol is added.

20. The method of claim 17 wherein the isoelectric point is from about pH 9.5 to about pH 10.

* * * * *